United States Patent
Arabi et al.

(10) Patent No.: US 12,150,848 B1
(45) Date of Patent: Nov. 26, 2024

(54) DEVICE, METHOD, AND SYSTEM FOR SPHINCTER CLOSING AND REOPENING TO TREAT INFERTILITY CAUSED BY RETROGRADE EJACULATION

(71) Applicant: UNITED ARAB EMIRATES UNIVERSITY, Al Ain (AE)

(72) Inventors: Alya A. Arabi, Al Ain (AE); Ali O. Arabi, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 18/653,658

(22) Filed: May 2, 2024

(51) Int. Cl.
*A61F 2/00* (2006.01)

(52) U.S. Cl.
CPC .......... *A61F 2/0018* (2013.01); *A61F 2/0036* (2013.01)

(58) Field of Classification Search
CPC .... A61F 2/0004; A61F 2/0018; A61F 2/0036; A61F 5/005; A61F 5/0056; A61F 5/0059; A61F 5/0069; A61F 5/0079; A61F 5/0083; A61F 5/0086
See application file for complete search history.

(56) References Cited

U.S. PATENT DOCUMENTS

| | | | |
|---|---|---|---|
| 8,734,475 B2 * | 5/2014 | Ekvall | A61B 17/08 606/157 |
| 10,398,440 B2 | 9/2019 | Kugler et al. | |
| 10,543,074 B2 * | 1/2020 | Frigstad | A61F 2/0036 |
| 10,945,738 B2 * | 3/2021 | Auld | A61B 17/12013 |
| 11,207,173 B2 * | 12/2021 | Popescu | A61F 5/0059 |
| 11,324,512 B2 | 5/2022 | Huster et al. | |

(Continued)

FOREIGN PATENT DOCUMENTS

| | | |
|---|---|---|
| CN | 102488571 B | 7/2014 |
| CN | 117442382 A | 1/2024 |
| EP | 1913904 A1 | 4/2008 |

OTHER PUBLICATIONS

Marziale, et al. "Artificial sphincters to manage urinary incontinence: a review." Artificial organs 42.9 (2018): E215-E233.

(Continued)

*Primary Examiner* — Carrie R Dorna
(74) *Attorney, Agent, or Firm* — Nath, Goldberg & Meyer; Joshua B. Goldberg (57) ABSTRACT

A device, system, and method for closing and reopening a sphincter in a body, such as for closing and opening an internal urinary sphincter of a bladder, thereby blocking retrograde ejaculation, by employing controllable electromagnets. Using the present device, system, and method, the patients can selectively close their bladder's sphincter as desired, for example, to selectively block retrograde ejaculation, preventing semen from entering the bladder of the patient and thereby preventing infertility of the patient. The solution helps regain the elasticity function of the sphincter to allow it to close as per normal to prevent retrograde ejaculation. A series of magnetizable metal objects are positioned in or surrounding the bladder wall at the junction with the urethra, with each of the magnetizable metal objects being electromagnetically controlled to have a controllable closing/reopening of the bladder's sphincter, thereby preventing retrograde ejaculation while also allowing the passage of urine as per normal.

20 Claims, 4 Drawing Sheets

(56) References Cited

U.S. PATENT DOCUMENTS

| | | |
|---|---|---|
| 11,559,385 B2 | 1/2023 | Berg et al. |
| 11,571,288 B2 | 2/2023 | Mazzocchi et al. |
| 2009/0062824 A1* | 3/2009 | Berg .................. A61F 5/005 600/12 |

OTHER PUBLICATIONS

Mazzocchi, et al. "Magnetically controlled endourethral artificial urinary sphincter." Annals of biomedical engineering 45 (2017): 1181-1193.

* cited by examiner

DEVICE, METHOD, AND SYSTEM FOR SPHINCTER CLOSING AND REOPENING TO TREAT INFERTILITY CAUSED BY RETROGRADE EJACULATION

BACKGROUND OF THE INVENTION

Field of the Invention

The disclosure of the present patent application relates to a device, method, and system for closing and reopening a sphincter in a body, such as for closing and opening an internal urinary sphincter of a bladder, thereby blocking retrograde ejaculation, by employing controllable electromagnets.

Description of Related Art

Due to various factors, more and more people are suffering from retrograde ejaculation. For example, surgeries like transurethral resection of the prostate (TURP), which is typically performed to remove enlarged prostate tissue that can press on the prostatic urethra, blocking the flow of urine, or in cases of benign prostate disease (BPD), have become commonplace. Unfortunately, the TURP surgery can damage the elasticity of the internal urethral sphincter given its proximity to the prostate gland, thereby potentially causing retrograde ejaculation. The elasticity of the bladder's sphincter can be further degraded due to aging, nerve loss, or other causes. The internal sphincter operates like a piece of rubber at the neck of the bladder which closes during ejaculation. The sphincter acts as a ring forming an opening in the bladder wall.

Figure 1:
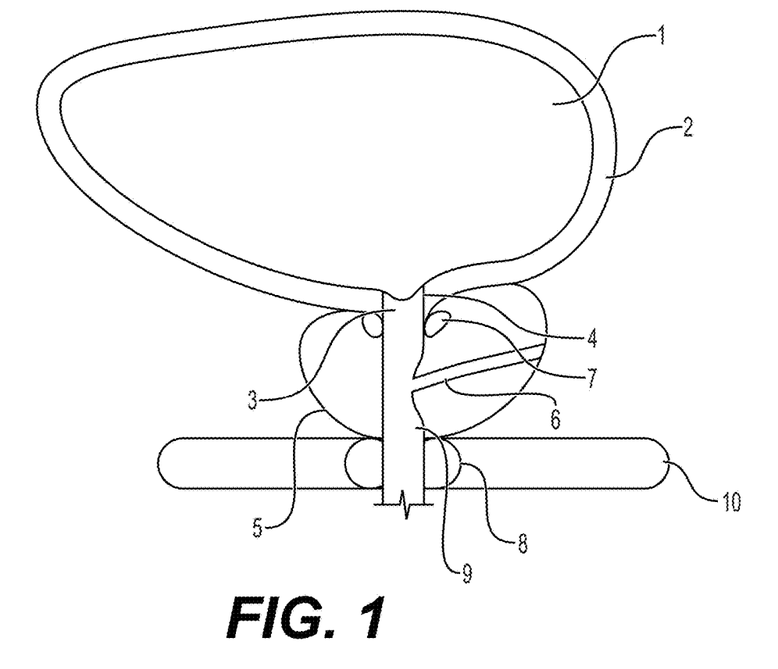
FIG. 1 shows a drawing of a bladder including a bladder wall as connected to a prostate, an internal urinary sphincter, and the like, with the bladder neck and an arrow demonstrating the positioning of the sphincter ring where the present device will be implanted.

In cases of retrograde ejaculation, semen released in the ejaculatory tract proceeds to the prostatic urethra where, instead of continuing to the membranous urethra and eventually through the bulbous urethra as would happen normally, it proceeds to enter the subject's bladder. This can occur due to damage to the internal sphincter of the bladder, i.e., the gatekeeper at the neck of the bladder, which is normally supposed to close to block this passage to the bladder. However, due to the damage, the sphincter loosens, thereby preventing the sphincter from fully closing to block this entry to the bladder and causing the retrograde ejaculation which, in turn, can cause undesirable infertility, as shown in FIG. 1 herein.

The currently available solutions to solve the problem of retrograde ejaculation are not ideal and can be improved. For example, retrograde ejaculation caused by medications such as alpha-blockers, antidepressants, or medications for high blood pressure, can be avoided by avoiding such medications. On the other hand, patients with weak muscles at the bladder neck can receive certain medications (e.g., Alpha-Adrenergic Agonists) in an attempt to alleviate the issue. However, such medications can cause side effects such as high blood pressure, rapid heart rate, anxiety, sleeping disorders, urinary retention, and the like.

In another alternative, surgeries can be done to restore the anatomy of the bladder neck. However, this option can be invasive, cause complications, can have a long recovery period, and has an uncertain success rate. Therefore, there is the need for finding better solutions for the problem of retrograde ejaculation.

SUMMARY OF THE INVENTION

The present subject matter relates to a device, system, and method for closing and reopening a sphincter in a body, such as for closing and opening an internal urinary sphincter of a bladder, thereby blocking retrograde ejaculation in a patient. Using the present device, system, and method, the patients can selectively close a sphincter as desired, such as the internal sphincter in their bladder to selectively block retrograde ejaculation, preventing semen from entering the bladder of the patient and thereby preventing infertility of the patient. The present device, system, and method can be used to selectively and controllably close and reopen any sphincter in a patient, not just the sphincter in the bladder.

The solution helps regain the elasticity function of the sphincter to allow it to close again and go back to its normal function, such as the normal function of blocking the retrograde ejaculation for the sphincter of the bladder. In this regard, two series of cylinders or vertical rods can be positioned in or through the wall of the bladder at the junction with the urethra such that they surround the sphincter of the bladder, with each of the series of cylinders or vertical rods being electromagnetically controlled to have a controllable closing of the sphincter of the bladder, thereby preventing retrograde ejaculation.

Accordingly, in an embodiment, the present subject matter relates to a method to solve the issue of retrograde ejaculation in a patient. This method can involve the closure of the internal sphincter, at the neck of the bladder, by electromagnetically activating a device implanted in a series of magnetizable metal objects around, whether internally or externally, a circumference of the internal sphincter.

In an embodiment, the present subject matter relates to a device for assisting in electromagnetically closing and reopening an internal urinary sphincter in a bladder of a patient, the device comprising: a series of magnetizable metal objects configured to surround a wall of the bladder around a circumference of the internal urinary sphincter in a bladder; an energy source comprising at least two batteries; and a series of wires connecting the at least two batteries to alternating magnetizable metal objects of the series of magnetizable metal objects to provide at least a first circuit and a second circuit, respectively, with each battery in each of the first circuit and the second circuit being connected to a single-pole, single-throw (SPST) switch, thereby providing at least two total switches, which, when each SPST switch is activated, each respectively completes at least a first electric circuit allowing a first electric current and a second electric circuit allowing a second electric current, respectively, to separately magnetize each magnetizable metal object; wherein the first circuit contains odd-numbered alternating magnetizable metal objects and the second circuit contains even-numbered alternating magnetizable metal objects as counted by starting from a first one of the alternating magnetizable metal objects which is considered alternating metal object number 1, the first metal object of the odd-numbered alternating magnetizable metal objects, the next one of the alternating magnetizable metal objects which is considered alternating metal object number 2, the first metal object of the even-numbered metal objects, and with each alternating metal object thereafter being among the odd-numbered alternating magnetizable metal objects or the even-numbered alternating magnetizable metal objects, accordingly; wherein when each SPST switch in each circuit is activated to enable an attraction mode, each of the odd-numbered alternating magnetizable metal objects are magnetized and each of the even-numbered alternating magnetizable metal objects are magnetized with attractive magnetic polarities such that each magnetizable metal object of the series of magnetizable metal objects are configured to be attracted to each other to close the internal urinary sphincter in a bladder, wherein the SPST in the second circuit is a delay-switch SPST; wherein the second circuit further comprises a single-pole, double-throw (SPDT) switch configured to reverse polarity of each of the even-numbered magnetizable metal objects in the second circuit to enable a repulsion mode in which each of the odd-numbered alternating magnetizable metal objects and each of the even-numbered alternating magnetizable metal objects are magnetized with repulsive magnetic polarities such that each magnetizable metal object of the series of magnetizable metal objects are configured to separate from one another to forcibly reopen the internal urinary sphincter in a bladder to the internal urinary sphincter's original open position; and wherein when each SPST switch in each circuit is deactivated to enable a rest mode, no electric current is conveyed to any of the magnetizable metal objects of the series of magnetizable metal objects.

In another embodiment, the present subject matter relates to a method for treating retrograde ejaculation in a patient, the method comprising: positioning a series of magnetizable metal objects to surround a wall of a bladder of the patient around a circumference of the internal urinary sphincter at the neck of the bladder; providing an energy source comprising at least two batteries to create at least a first electric current and a second electric current, respectively, to magnetize each magnetizable metal object; connecting the at least two batteries to alternating magnetizable metal objects of the series of magnetizable metal objects to provide at least a first circuit and a second circuit, respectively, the first circuit containing odd-numbered alternating magnetizable metal objects and the second circuit containing even-numbered alternating magnetizable metal objects as counted by starting from a first one of the alternating magnetizable metal objects which is considered alternating metal object number 1, the first metal object of the odd-numbered alternating magnetizable metal objects, the next one of the alternating magnetizable metal objects which is considered alternating metal object number 2, the first metal object of the even-numbered metal objects, and with each alternating metal object thereafter being among the odd-numbered alternating magnetizable metal objects or the even-numbered alternating magnetizable metal objects, accordingly, to provide the first electric current to each of the odd-numbered alternating magnetizable metal objects in the first circuit and the second electric current to each of the even-numbered alternating magnetizable metal objects in the second circuit; selectively activating a single-pole, single-throw transfer switch (SPST) connected to batteries in each of the first circuit and the second circuit to enable an attraction mode to provide the first electric current to each odd-numbered alternating magnetizable metal object and to provide the second electric current to each even-numbered alternating magnetizable metal object, thereby alternately magnetizing each odd-numbered alternating magnetizable metal object and each even-numbered alternating magnetizable metal object with attractive magnetic polarities such that each magnetizable metal object of the series of magnetizable metal objects are attracted to each other to close the internal urinary sphincter in the bladder and prevent the retrograde ejaculation; if necessary, selectively activating each SPST connected to the batteries in each of the first circuit and the second circuit while reversing polarity of each of the even-numbered alternating magnetizable metal objects by flipping a single-pole double-transfer (SPDT) switch, to enable a repulsion mode to magnetize each of the odd-numbered alternating magnetizable metal objects and each of the even-numbered alternating magnetizable metal objects with repulsive magnetic polarities such that each magnetizable metal object of the series of magnetizable objects separates from one another to forcibly reopen the internal urinary sphincter of the bladder, thereby allowing urine to exit the bladder; and selectively deactivating each SPST switch connected to the batteries in each of the first circuit and the second circuit to release the electric current such that each magnetizable metal object of the series of magnetizable metal objects demagnetize, permitting the magnetizable metal objects to remain in the open position if the repulsion mode was enabled before the rest mode, or to move apart from one another due to a change in ambient conditions that pull the internal urinary sphincter of the bladder to an open position in case the repulsion mode was not enabled before the rest mode, thereby reopening the internal urinary sphincter in the bladder.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

When the magnetized metal cylinders are described herein as maintaining a "relatively constant position" inside the wall of the body part, or bladder, and navigating along the circumference of the sphincter of the body part, or the internal urinary sphincter of the bladder, with little to no movement, particularly in relation to one another, such that each magnetized metal cylinder is continuously essentially equidistant, one from the other. Further, each magnetized metal cylinder will have little to no opportunity to shift in an equidistant position from the others along the circumference of the wall of the body part.

As used herein, when magnetizable metal objects are said to have "attractive magnetic polarities" this indicate that the portions of the magnetizable metal objects closest to one another have opposite magnetic polarities such that they attract one another. For example, in the rods embodiment as described herein, alternating rods with opposite net magnetic dipoles will attract, one to the next, because they are vertically inserted through the sphincter and thus will always have a same orientation, while, similarly, alternating rods with the same magnetic dipoles will repel, one from the next. However, for the cylinders embodiment as described herein, alternating cylinders with opposite net magnetic dipoles will repel, one to the next, because they are horizontally placed one after the other and, as such, cylinders with opposite magnetic dipoles repel one another and alternating cylinders with common net magnetic dipoles will attract, one to the next, because they are horizontally placed one after the other and, as such, cylinders with common magnetic dipoles attract one another.

The present subject matter relates to a device, system, and method for closing and reopening a sphincter in a body, such as for closing and opening an internal urinary sphincter of a bladder, thereby blocking retrograde ejaculation in a patient. Using the present device, system, and method, the patients can selectively close a sphincter as desired, such as the internal sphincter in their bladder to selectively block retrograde ejaculation, preventing semen from entering the bladder of the patient and thereby preventing infertility of the patient.

For the avoidance of doubt, the present device, system, and method can be used to selectively and controllably close and reopen any sphincter in a patient, not just the sphincter in the bladder. Accordingly, the replacement of any instance of "internal urinary sphincter" and "bladder" herein with another sphincter and body part is contemplated as included within the scope of the present subject matter.

The solution helps regain the elasticity function of the internal urinary sphincter to allow it to close as it normally would to prevent retrograde ejaculation. In this regard, a series of magnetizable metal objects, such as horizontal magnetizable metal cylinders and/or vertical magnetizable metal rods, can be positioned in or surrounding the wall of the bladder at the junction with the urethra, with each of the series of magnetizable metal objects being electromagnetically controlled to have a controllable closing of the sphincter of the bladder, thereby preventing retrograde ejaculation.

In an additional embodiment, the controllable closing/reopening of the sphincter of the bladder can be used to prevent urinary incontinence and/or leakage by closing the sphincter of the bladder as desired, thereby preventing any urine from leaking therethrough.

Accordingly, in an embodiment, the present subject matter relates to a method to solve the issue of retrograde ejaculation in a patient. This method can involve the closure of the internal sphincter, at the neck of the bladder, by electromagnetically activating a device implanted in a series of magnetizable metal objects around, whether internally or externally, a circumference of the internal urinary sphincter. As described herein, the present methods can involve a controllable closure and reopening of the internal sphincter via a three-mode model, where the first mode is "attraction", the second mode is "repulsion", and the third mode is "rest".

In this regard, to treat retrograde ejaculation, the present device can be implanted within the bladder wall (2) as seen by referring to current FIG. 1, showing a drawing of a bladder (1) including a bladder wall (2) as connected to a prostate (5), an internal urinary sphincter (3), an internal urethral sphincter (7), an external urethral sphincter (8), a prostate urethra (9), a deep perineal pouch (10), and an ejaculation duct (6) through which semen passes to be expelled from the body, the bladder neck (4) and an arrow demonstrating the positioning of the sphincter ring show where the present device will be implanted.

Figure 2A:
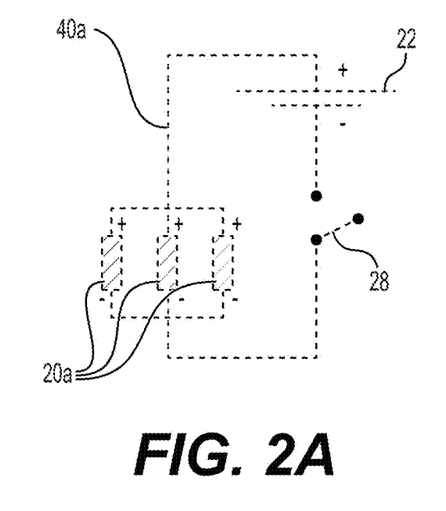
FIG. 2A shows the first circuit embodiment of the present subject matter, i.e., the embodiment of the first circuit connecting a first battery to odd-numbered alternating magnetizable metal objects, in parallel, and a single-pole, single-throw (SPST) switch.
Figure 2B:
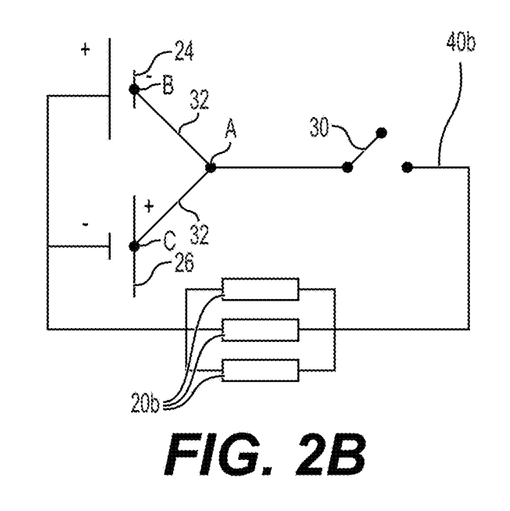
FIG. 2B is a circuit drawing showing the second circuit embodiment of the present subject matter with a second circuit connecting a second battery and a third battery to the even-numbered alternating magnetizable metal objects, in parallel, and both an after delay single-pole, single-throw (SPST) switch and a single-pole, double-throw (SPDT) switch having A, B, and C terminals.
Figure 2C:
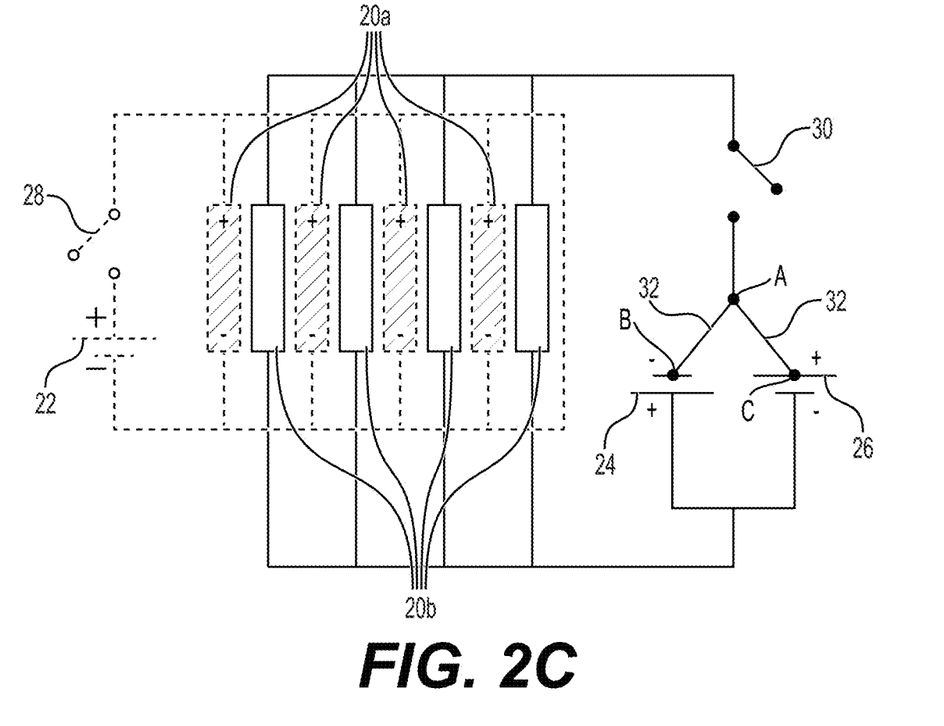
FIG. 2C is a circuit drawing showing a "set" of two-circuit embodiment with circuit 1 and circuit 2, as represented by first and second circuit embodiments as shown in FIGS. 2A and 2B, respectively, taken together as one set.

In this regard, the "attraction" mode can close the internal urinary sphincter by electromagnetically attracting the magnetizable metal objects which become magnetizable once an electric current passes therethrough, for example, as shown in each of the two circuits of FIG. 2C. In the "attraction" mode, the magnetizable metal objects can become uniformly magnetized, resulting in the establishment of opposite magnetic polarities across neighboring magnetizable metal objects (e.g., NSNSNS . . . ). Consequently, the north pole of one magnetizable metal object can attract the south pole of adjacent magnetized metal objects, forming a sequential (linear or circular) alignment.

Conversely, in the "repulsion" mode, the magnetizable metal objects can become magnetized with repulsive magnetic polarities (e.g., NSSNNSSN . . . ). This configuration can lead to the repulsion of the north pole of one magnetized metal object from the north pole of the neighboring magnetized metal objects, generating a series of repulsive interactions across the series of the magnetized metal objects.

After the internal urinary sphincter is closed by the electromagnet attraction of the magnetized metal objects, the electric currents can be switched off and the magnetized metal objects are expected, in the absence of an electromagnetic force, to be separated by 1) the normal anatomical features and physiological process that pull the internal urinary sphincter back to the open position, or by 2) the pressure of urine. However, should neither the anatomical/physiological process nor the pressure of urine be sufficient to repel the magnetizable metal objects, then the "repulsion" mode can be entered to forcibly repel the magnetizable objects until reaching the default original internal urinary sphincter opening. If either of the two separation conditions, or their combination, is sufficient to reopen the internal urinary sphincter opening, then the "repulsion" mode could be skipped. That is, it will be possible to go straight from the "attraction" mode to the "rest" mode, with no need to use the "repulsion" mode at any step of the process.

The "rest" mode can occur when the magnetizable metal objects are not magnetized and they are in their original position as they were originally in the open internal urinary sphincter before entering the "attraction" mode.

Accordingly, in an embodiment, the present subject matter relates to a device and a method for assisting in closing and reopening an internal urinary sphincter in a bladder of a patient, the device comprising: a series of magnetizable metal objects configured to surround a wall of the bladder around a circumference of the internal urinary sphincter in the bladder; an energy source comprising at least two batteries connected to alternating magnetizable metal objects of the series of magnetizable metal objects to provide at least a first circuit and a second circuit, respectively, with each battery in each of the first circuit and the second circuit being connected to a single-pole, single-throw (SPST) switch, thereby providing at least two total switches, which, when each SPST switch is activated, each respectively completes at least a first electric circuit allowing a first electric current and a second electric circuit, respectively, to separately magnetize each magnetizable metal object; a series of wires connecting the at least two batteries to alternating magnetizable metal objects of the series of magnetizable metal objects to provide the first and second electric currents to respective first and second electric circuits, with each battery in each of the first circuit and the second circuit being connected to a single-pole, single-throw (SPST) switch, thereby providing at least two total switches.

In certain embodiment, each of the series of wires connecting the at least two batteries to alternating magnetizable metal objects of the series of magnetizable metal objects can be covered with an insulating layer of biocompatible material to avoid causing an electric shock to the patient after implantation and during use.

In this regard, the second circuit can optionally further comprises a single-pole, double-throw (SPDT) switch configured to reverse polarity of each of the even-numbered magnetizable metal objects in the second circuit to enable a repulsion mode in which each of the odd-numbered alternating magnetizable metal objects and each of the even-numbered alternating magnetizable metal objects are magnetized with repulsive magnetic polarities such that each magnetizable metal object of the series of magnetizable metal objects are configured to separate from one another to forcibly reopen the internal urinary sphincter in the bladder to the sphincter's original open position The at least two total switches, with at least one switch in each circuit, when suitably activated are responsible for enabling the "attraction", "repulsion", or "rest" mode of the presently described device. In this regard, the at least two total switches can be selectively activated to provide the electric current to respective odd-numbered and even-numbered alternating magnetizable metal objects of the series of magnetizable metal objects so that each magnetizable metal object of the series of magnetizable metal objects are separately magnetized.

When each SPST switch in each circuit is activated to enable an attraction mode, each of the odd-numbered alternating magnetizable metal objects can be magnetized and each of the even-numbered alternating magnetizable metal objects can be magnetized with attracting magnetic polarities such that each magnetizable metal object of the series of magnetizable metal objects can be configured to be attracted to each other to close the internal urinary sphincter in the bladder.

When the second circuit further comprises a single-pole, double-throw (SPDT) switch configured to reverse polarity of each of the even-numbered magnetizable metal objects in the second circuit to enable a repulsion mode in which each of the odd-numbered alternating magnetizable metal objects and each of the even-numbered alternating magnetizable metal objects can be magnetized with repulsive magnetic polarities such that each magnetizable metal object of the series of magnetizable metal objects can be configured to separate from one another to forcibly reopen the internal urinary sphincter in the bladder to the sphincter's original open position, i.e., the default opening.

When teach SPST switch in each circuit is deactivated to enable a rest mode, no electric current is conveyed to any of the magnetizable metal objects, allowing the magnetizable metal objects to be apart from one another due to a change in ambient conditions as described herein. In this regard, the ambient conditions can vary depending on the specific sphincter being treated. By way of non-limiting example, for an internal urinary sphincter, the ambient conditions can include a relaxing of the internal urinary sphincter, build-up of pressure due to collection of urine in the bladder, and the like.

In this regard, the magnetizable metal objects as used and described herein can be either magnetizable metal rods inserted through the body part wall, i.e., through the bladder wall around the circumference of the neck of the bladder and perpendicular to the plane of the sphincter, or the magnetizable metal objects can be magnetizable metal cylinders embedded horizontally within the body part wall of the around the circumference of the neck of the body part.

In one embodiment, each of the magnetizable metal objects in the series of magnetizable metal objects can be magnetizable metal cylinders in a series of magnetizable metal cylinders and can be configured to be embedded inside the wall of the bladder and navigate along the circumference of the internal urinary sphincter in the bladder. In this regard, each of the cylinders can be implanted into the patient through a small incision, where all cylinders are pushed through one side either into the wall of the sphincter, or to progress through the wall of the sphincter. The respective cylinders can be pushed until inside the body part wall and around the sphincter such that they surround the sphincter.

In certain embodiments in this regard, the magnetizable metal cylinders can comprise an even number of eight or more magnetizable metal cylinders. For example, the series of cylinders can comprise eight, ten, twelve, or more cylinders, respectively. The usage of this even number of cylinders in certain embodiments can aid in the compression of the device herein.

In one embodiment, the equal, even number of eight or more cylinders can be configured to maintain the device, when at rest, in a ring configuration navigating along the circumference of the internal urinary sphincter in the bladder. In one embodiment in this regard, the even number of eight or more cylinders can be placed such that they are maintained equidistant from one another surrounding the internal urinary sphincter in the bladder. The same "equidistant" configuration can be employed for the rods embodiment in addition to the cylinders embodiment.

In the cylinders embodiment, when each SPST switch in each circuit is activated to enable the attraction mode, a first set comprising a first half of each of odd-numbered and even-numbered alternating magnetizable metal cylinders of the series of magnetizable metal cylinders can magnetize together to form a first line magnetized in a north-to-south direction and a second set comprising a second half of each of odd-numbered and even-numbered alternating magnetizable metal cylinders of the series of magnetizable metal cylinders can magnetize together to form a second line magnetized in a south-to-north direction; wherein the first line and the second line can be configured to be attracted to each other to linearly close the internal urinary sphincter in the bladder. In this regard, the first set and the second set can each comprise separate first and second circuits, respectively.

In other words, the magnetizable metal cylinders close linearly via three steps: 1) the series of cylinders in one semi-circumference can be uniformly magnetized to attract linearly with a net magnetic dipole of N to S, 2) the series of cylinders in the other semi-circumference can be uniformly magnetized to attract linearly with a net magnetic dipole of S to N, 3) the opposite polarities of the two lines attract them to each other and the two lines of the two semi-circumferences of the sphincter close linearly.

Further, each of the first set of each magnetizable metal cylinder and the second set of each magnetizable metal cylinder can be configured to define first and second semi-circular portions of the device, respectively. Each of the first and second semi-circular portions of the device can be configured to be positioned around a first half and a second half of the circumference of the internal urinary sphincter in the bladder, respectively. That is, each of these semi-circular portions can be considered as separate sets, with the cylinders embodiment constituting two sets of magnetizable metal cylinders. Further, each separate set should have an equal number of cylinders, for example four cylinders each, for a total of eight cylinders. Additionally, each semi-circular portion should be connected to a different set of at least two batteries to magnetize alternating metals.

The bladder membrane, or the wall of the bladder, of the typical patient is usually about 2 mm to about 4 mm thick. Accordingly, in an embodiment, each magnetizable metal cylinder can have a diameter of up to 1.5 mm, about 1.5 mm, or up to about 1.5 mm. In other embodiments, each magnetizable metal cylinder can be appropriately sized depending on the thickness of the wall of the body part being treated.

Further, each magnetizable metal cylinder should be lightweight to avoid pulling the sphincter downward. By way of comparison, bladder stones can each be a few grams to several tens of grams. The magnetizable metal cylinders herein should have a mass lower than that of such bladder stones.

In one embodiment, each cylinder of the first series of cylinders can be configured to be located inside the wall of the bladder and navigating along the first half of the circumference of the internal urinary sphincter in the bladder and each cylinder of the second series of cylinders can be configured to be located inside the wall of the bladder and navigating along the second half of the circumference of the internal urinary sphincter in the bladder. That is, each of the cylinders can be inserted, positioned, placed, and/or located inside the wall of the bladder and surrounding the internal urinary sphincter in the bladder. According to this configuration, the device can operate via linear compression, like the closing of an ellipse. In this regard, in each semi-circle, the cylinders can be first magnetized together to form two lines. The two lines can then be attracted to each other to close the internal urinary sphincter without any extra electric or magnetic field, but instead based only on proximity of the two lines to one another and by the attraction of the two lines having opposite polarities, as the lines can have a net magnetic dipole of north-to-south in one line and south-to-north in the other line.

In another embodiment, each of the magnetizable metal objects in the series of magnetizable metal objects can be magnetizable metal rods in a series of magnetizable metal rods and can be configured to be inserted through the wall of the bladder perpendicular to a plane of the internal urinary sphincter and navigating along the circumference of the internal urinary sphincter in the bladder. In certain embodiments in this regard, the magnetizable metal rods can comprise an even number of eight or more magnetizable metal rods.

In the rods embodiment, when the at least one switch in each circuit is activated to enable the attraction mode, each magnetizable metal rod of the series of magnetizable metal rods can be configured to be attracted focally to a center to close the internal urinary sphincter in the bladder. In this regard, all rods employed in the present devices can be considered as one set of magnetizable metal rods, or one set of magnetizable metal objects.

In certain embodiments, each of the magnetizable metal rods can be configured to stick out of the wall of the bladder by about 1 mm on each side. In further embodiments, each of the magnetizable metal rods can have a stopper on each side of the wall so that each of the magnetizable metal rods can be configured to have a fixed position and can be configured to not be displaced from their position sticking through the wall of the bladder. In certain embodiments in this regard, the magnetizable metal rods configured for implantation in and sticking out of the wall of the bladder can be provided with one stopper fixed on one end of the metal rods with a second stopper configured to be placed on/come off the other end of the metal rods to a perpendicular position to the each rod after each rod is inserted through the wall of the bladder.

Switching the electric currents off or on is controlled by the opening or closing of the switch in each respective current, which can be controlled by the patient as described herein. Therefore, to avoid retrograde ejaculation, just before copulation, the patient can activate each SPST switch to permit electric current to pass through each of the first and second circuits, thereby ensuring that the magnetizable metal objects are closed. Once ejaculation is complete, the electricity can be switched off, the magnetizable metal objects are no longer attracted, and the internal urinary sphincter would be capable of opening as the elasticity in the internal sphincter in the patient is lost or even due to ambient conditions, such as, by way of non-limiting example, the pressure of the urine in the bladder.

However, should the internal urinary sphincter still not reopen after the electric currents are switched off to permit urine passage, the magnetizable metal objects can be separated by magnetization of the magnetizable metal objects with repulsive magnetic metal polarities, thereby enabling a repulsion mode. This repulsion can happen by applying the repulsive magnetic polarities to alternating magnetizable metal objects. For example, if the pole is north-to-south in one magnetized metal rod or cylinder, the neighboring magnetized metal rod has to be also north-to-south and the neighboring magnetizable metal cylinder has to be south-to-north. The neighboring magnetizable metal objects can each be connected to an SPDT switch to allow selectively creating a north-to-south vs. a south-to-north electromagnet by having clockwise vs. anticlockwise currents. After repulsion, the batteries can be turned off, and the sphincter can remain open by default. For example, leaving the internal urinary sphincter open means the urine can pass from the bladder to the prostatic urethra.

If the patient has a properly functioning external sphincter, for example, the sphincter of a bladder, this will block any further involuntarily leakage of urine, but if the external sphincter happens to also be damaged (for whatever reason), then the patient would suffer from the issue of involuntarily urine leakage. This issue can be solved by maintaining the device closed by default, and the patient can controllably reopen it to its original opening for urination.

In an embodiment, the present device design provides the ability to close and reopen the device, thereby fully controlling when the retrograde ejaculation can be prevented or when the urine can be passed out.

In another embodiment, the magnetizable metal objects themselves are not magnets, but instead are made of a magnetizable metal. In this regard, an electric current can be applied to the objects to magnetize them. In one embodiment in this regard, all objects used in the devices herein can be made of the same magnetizable metal such as, by way of non-limiting example, a martensitic stainless steel such as F138 stainless steel or a cobalt-chromium alloy. The martensitic stainless steel used herein is a type of stainless-steel alloy known for its high strength, hardness, and magnetic properties. The microstructure of the material used in this regard can contribute to its magnetic properties.

A non-magnetizable metal, such as an austenitic stainless steel, cannot be used herein. In another embodiment in this regard, the magnetizable metal used herein can be made of a biocompatible metal.

When each switch in each circuit is activated to enable the repulsion mode, each of the odd-numbered alternating magnetizable metal objects can be magnetized and each of the even-numbered alternating magnetizable metal objects can be magnetized with attractive magnetic polarities such that each magnetizable metal object of the series of magnetizable metal objects can be configured to be attracted to each other to close the internal urinary sphincter in the bladder. In this regard, the SPST in the second circuit can be a delay-switch SPST.

In certain embodiments, the second circuit can further comprise a single-pole, double-throw (SPDT) switch which can permit the electric current to switch from flowing from the second battery to the third battery to every even-numbered alternating magnetizable metal object of the series of magnetizable metal objects starting with the second magnetizable metal object in a same or opposite direction of the flow of electric current from the first battery such that each magnetizable rod or cylinder of the series of magnetizable metal objects, respectively, can be separated from one another to forcibly reopen the internal urinary sphincter of the bladder.

Referring to the figures, in the device, the three batteries in each "set" of the series of magnetizable metals can be connected as follows.

Figure 3A:
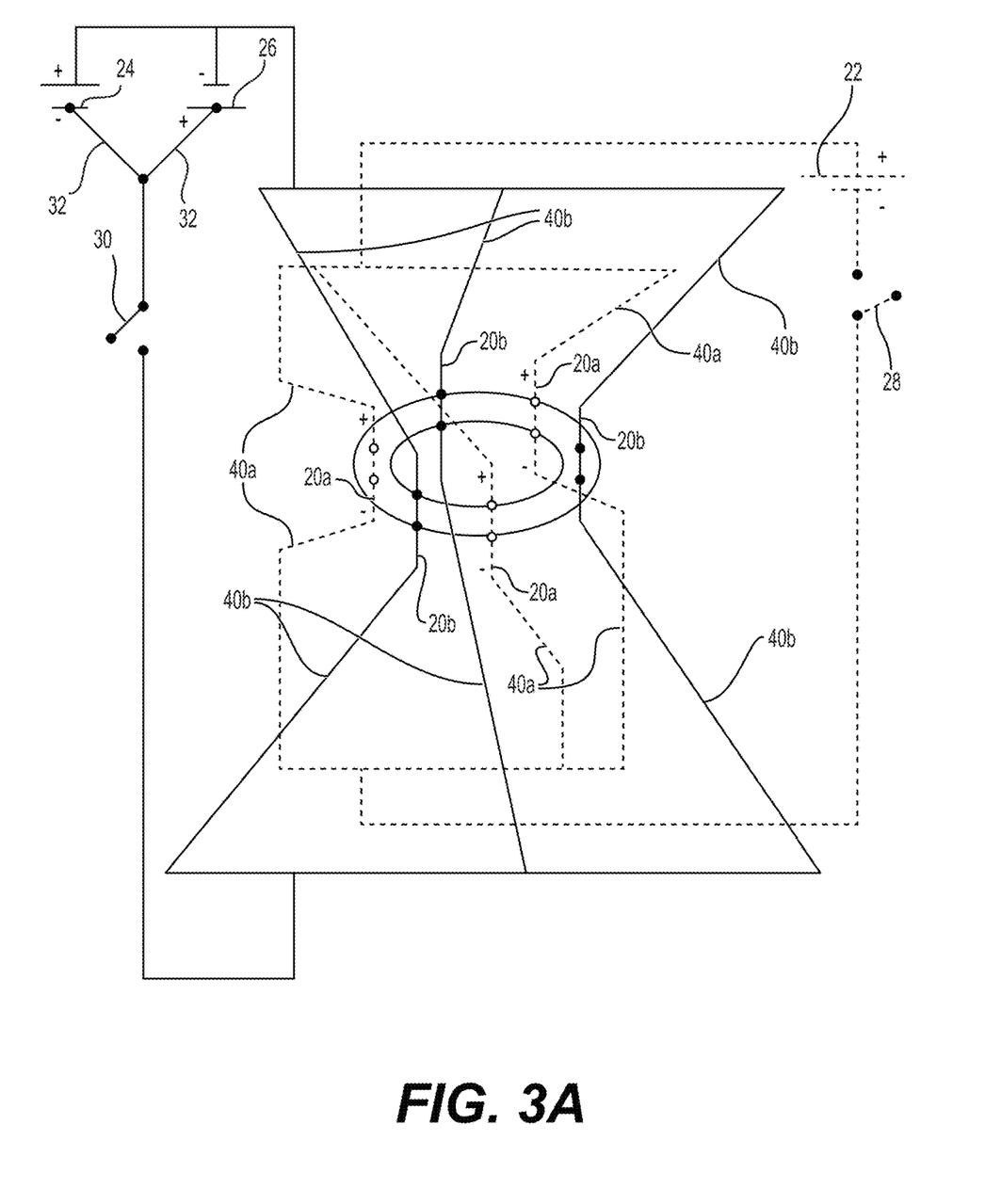
FIG. 3A is a drawing of a rod embodiment of the present subject matter, wherein each rod, with two stoppers, is inserted vertically through the wall of the bladder perpendicular to a plane of the internal urinary sphincter and navigating along the circumference of the internal urinary sphincter of the bladder.
Figure 3B:
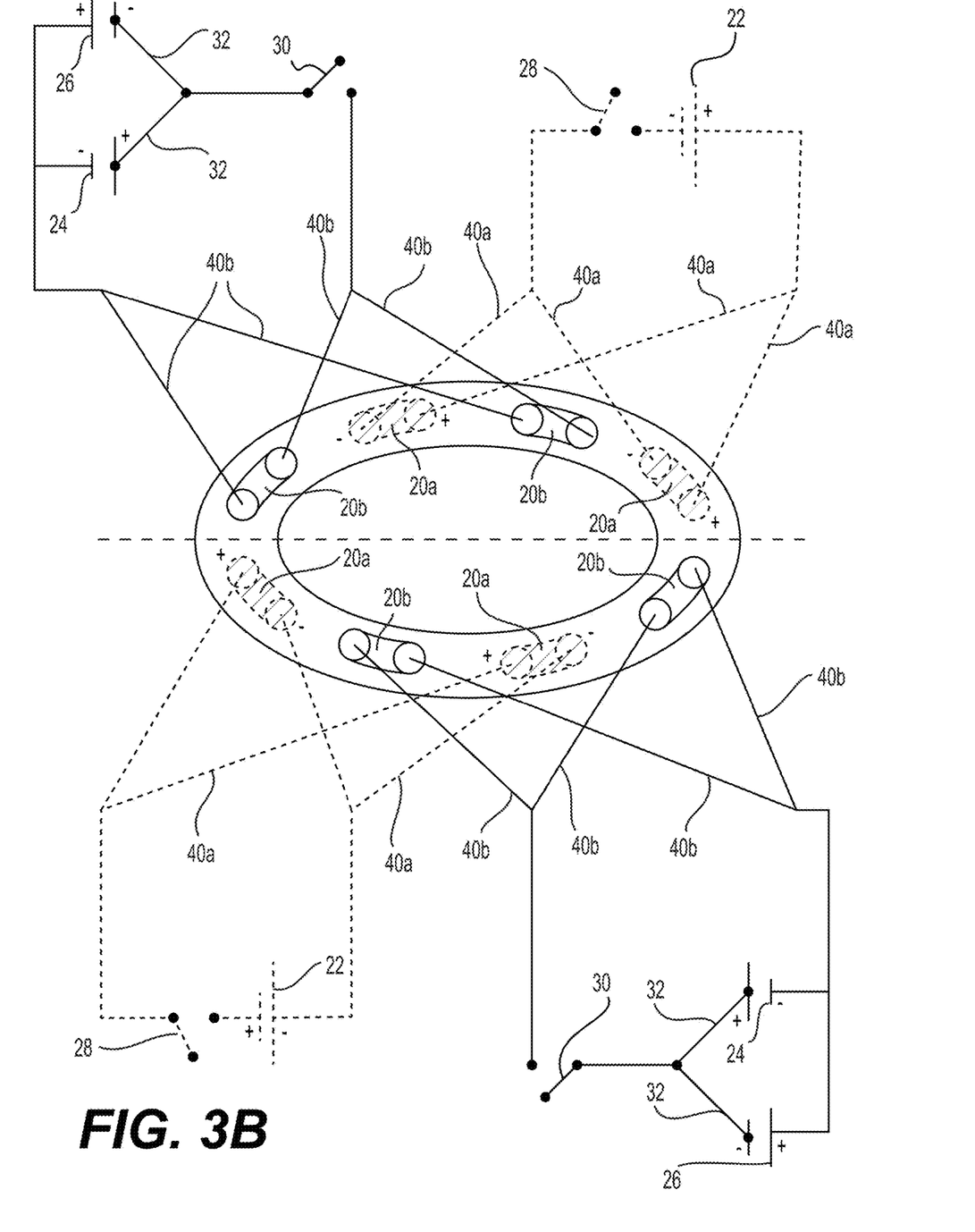
FIG. 3B is a drawing of a cylinder embodiment of the present subject matter, wherein each cylinder is embedded inside the wall of the bladder, with the cylinders forming two sets as delineated, one from the other, by the dashed line separating the two sets.

Circuit 1 with battery 1, as shown in FIG. 2A and the circuit with dotted lines in FIG. 2C: starting with one magnetizable metal object (e.g. magnetizable metal object #1 (20a)), every second magnetizable metal object (20a) is connected to this battery (22), in parallel, using wires (40a) as shown in FIGS. 3A and 3B. In other words, if the magnetizable metal objects (20) are numbered sequentially, all magnetizable metal objects with odd numbers (20a) are connected, in parallel, to this battery (22) via wires (40a). This battery (22) is shown in FIG. 2A and FIG. 2C to allow a conventional current flow direction in the circuit from positive to negative when the SPST switch 28 is activated, i.e. flipped to the "on" position. In certain embodiments, the electric current can flow in a direct opposite to that of the conventional current flow. According to these embodiments, all other directions, polarities, etc. will likewise be flipped in an opposite manner accordingly.

Circuit 2 with batteries 2 and 3, as shown in FIG. 2B and the circuit with solid lines in FIG. 2C: starting with the next consecutive magnetizable metal objects (i.e. magnetizable metal object #2 (20b)), every second magnetizable metal object (20b) is connected to one of the two batteries (24, 26), in parallel, using wires (40b) as shown in FIGS. 3A and 3B. In other words, if the magnetizable metal objects (20) are numbered sequentially, all magnetizable metal objects with even numbers (20*b*) are connected, in parallel, to one of the two batteries (24, 26) via wires (40*b*). The current flow direction here can be from positive to negative (conventional current flow) or from negative to positive (i.e. opposite current flow) depending on which of battery 2 (24) or battery 3 (26) is used.

In Circuit 2, as shown in FIG. 2B and the circuit with solid lines in FIG. 2C, there is a "single-pole, double-throw (SPDT) switch" (32) as described herein that can control the electric current flow from the two batteries (24, 26). The SPDT switch (32) has three terminals as shown in FIG. 2B and FIG. 2C: a common terminal (A), and two other terminals (B and C) which can be alternatively connected to the common terminal depending on the switch position. Also included in Circuit 2 is an after-delay SPST switch (30).

When the SPDT switch (32) connects Terminal A (as shown in FIG. 2B and FIG. 2C) to Terminal B (as shown in FIG. 2B and FIG. 2C) and Terminal C (as shown in FIG. 2B and FIG. 2C) is disconnected, the current will flow from Terminal B through Terminal A and into the circuit (this is from negative to positive current flow according to FIG. 2B and FIG. 2C). When the SPDT switch (32) is flipped to the other position, Terminal C is connected to Terminal A, as shown in FIG. 2B and FIG. 2C (and Terminal B is disconnected). This reverses the direction of current flow, causing it to flow from Terminal C through Terminal A, as shown in FIGS. 2B and 2C, taken in combination, and into the circuit (this is the conventional current flow from positive to negative, according to the FIG. 2A). Therefore, by flipping the SPDT switch (32), it is possible to effectively reverse the current flow in the circuit.

In a further embodiment, the electric currents applied to alternating ones of the first series of cylinders and the second series of cylinders can be reversible electric currents to enable reopening of the device, such reopening extending to the full original circumference of the sphincter being reopened. This can be achieved via each SPST switch in each circuit, or microswitches, which can manage the delivery of the currents to the respective objects. In certain embodiments, all switches used can be placed internally in the patient, for example, in a location near or with the batteries.

At rest, the electric currents of both circuits are switched off. When the patient wishes to block retrograde ejaculation, they can switch the electric currents on, thereby closing the sphincter of the bladder and preventing retrograde ejaculation. This can further prevent infertility in the patient.

In certain embodiments, the at least two batteries can comprise three batteries configured such that every second magnetizable metal object of the series of magnetizable metal objects starting with a first magnetizable metal object can be connected to a first battery of the three batteries, in parallel. Further, every second magnetizable metal object of the series of magnetizable metal objects starting with a second magnetizable metal object adjacent to the first magnetizable metal object can be connected, in parallel, to a second battery or a third battery of the three batteries. The advantage of using the second battery or third battery is that it can allow for the use of different voltages (as desired) for the different batteries.

In this regard, typically, the power source (such as a battery or power supply) is connected to the common terminal of the SPDT switch. One of the other terminals would be connected to one lead of the magnetizable metal objects, while the other terminal would be connected to the other lead of the magnetizable metal objects. When this SPDT switch is in one position, the circuit will be in one direction, and when the SPDT switch is in the other position, the circuit will be in the opposite direction.

According to this three-battery configuration, the at least one switch in each circuit can comprise both a first and a second single-pole, single-throw (SPST) switch in the first and second circuits, respectively, and a single-pole, double throw (SPDT) switch in the second circuit. In this regard, the first single-pole, single-throw (SPST) switch can connect the first battery to every second magnetizable metal object of the series of magnetizable metal objects starting with the first magnetizable metal object, while the second single-pole, single-throw (SPST) switch, which is an after-delay SPST switch (30) can connect the second battery or the third battery to every second magnetizable metal object of the series of magnetizable metal objects starting with the second magnetizable metal object. Similarly, the single-pole, double-throw (SPDT) switch can be connected to each of the second battery and the third battery, thereby controlling flow of the electric current to every second magnetizable metal object of the series of magnetizable metal objects starting with the second magnetizable metal object.

When the at least one switch in each circuit is activated to enable the attraction mode, the single-pole, single-throw (SPST) switch can permit the electric current to flow from the first battery to every second magnetizable metal object of the series of magnetizable metal objects starting with the first magnetizable metal object. Further, the single-pole, double-throw (SPDT) switch can permit the electric current to flow to every even-numbered alternating magnetizable metal object of the series of magnetizable metal objects with attractive metal polarities such that each magnetizable rod of the series of magnetizable metal objects can be attracted to each other to close the internal urinary sphincter in the bladder, or with repulsive metal polarities such that each magnetizable cylinder of the series of magnetizable metal objects can be repelled from one other to open the internal urinary sphincter in the bladder.

In addition, for the repulsion mode, the SPDT can convert from the second battery to the third battery to provide an opposite direction electric current to the even-numbered alternating magnetizable metal objects to repel all magnetizable rods from one another and attract all magnetizable cylinders to each other.

When the at least one switch in each circuit is deactivated to enable the rest mode, the first single-pole, single-throw (SPST) switch can prevent the electric current from flowing from the first battery to every second magnetizable metal object of the series of magnetizable metal objects starting with the first magnetizable metal object. Likewise, the second single-pole, single-throw (SPST) switch can prevent the electric current from flowing from the second battery or the third battery to every second magnetizable metal object of the series of magnetizable metal objects starting with the second magnetizable metal object. This can allow the magnetizable metal objects to remain apart after the repulsion mode has been enabled.

Circuit 1 with battery 1 can have a single-pole, single-throw (SPST) switch to connect or disconnect the current.

Circuit 2 with batteries 2 and 3 can have an "after-delay single-pole, single-throw (SPST) switch" to connect the current (enabling the activation mode provided that the SPST of circuit 1 is also activated) or to disconnect the current after the SPDT switches from one battery to another, in other words enabling the repulsion mode followed by enabling the rest mode.

In certain embodiments, batteries 2 and 3 can be reduced to one battery (e.g., only battery 2), and an automatic switch can be used to reverse the current flow by using battery 1 and battery 2 vs. battery 1 and battery 1. In other words, the at least two batteries in this embodiment comprises two batteries, and wherein battery 1 is configured to replace electrical current provided by battery 3 to instead be provided by battery 1, thereby enabling the repulsion mode.

It is to be noted that, according to one possible feature, in all the embodiments described above, each battery used and described herein can be separate from the bladder and sphincter of the patient, such that any batteries can be placed under the skin of the patient to enable easy recharging or replacement, as needed. In this regard, the batteries can be configured for wireless charging or for easy replacement, similar to the procedure currently used with a pacemaker. That is, each battery can be configured such that the battery can be placed subcutaneously in the patient. In certain embodiments, each battery can be a wirelessly rechargeable battery or a replaceable battery.

The limitation of the longevity of the battery used herein can be bypassed by having a battery like that used for a heart pacemaker or other alternatives. In this regard, the battery can be located just under the skin so it can be easily recharged wirelessly, or even replaced with a small incision. In certain embodiments, each battery used herein can be a 1.5 V battery. In other embodiments, each battery used herein can be a 3.0 V battery (or a higher voltage battery as needed) if a stronger field is needed.

In additional embodiments, the battery and switch can be operated via a wireless remote control, Bluetooth®, or through a wirelessly connected cellphone, i.e., through an external control device. The external control device could be an arm band, Bluetooth, or a remote sensor. In an embodiment, the external control device can switch the electric current on and off. If the "ON" button of the external device is pressed, the electric current is supplied to the cylinders, which are then magnetized into the attraction mode to close the sphincter. If the "OFF" button of the external device is pressed, the electric current is first supplied to the magnetizable metal objects, which are then magnetized into the repulsion mode to open the sphincter, and then the electric current is no longer supplied to the magnetizable metal objects, which are then demagnetized into the rest mode to keep the sphincter in its original open position without an electromagnet.

According to the "ON" embodiment, the SPST switch of circuit 1 can be closed, meaning that the current flow is on (in the conventional current flow direction) and all the magnetizable metals with odd numbers are magnetized with the same polarity; and the SPST switch in circuit 2 is closed meaning that the current flow is on, and, in addition, the SPDT is connecting A to B (i.e. current flow from negative to positive). All the magnetizable metals with even numbers are magnetized with the same polarity, which is opposite to the polarity of the magnetizable metals in circuit 1 (i.e. magnetizable metals with odd numbers, in this case according to the FIG. 2C). This way each consecutive magnetizable metal objects are magnetized with opposite polarities and are, therefore, attracted to each other if rods or repelled from one another if cylinders.

The other button "OFF" corresponds to the "repulsion" mode of the method followed by the "rest" mode of the method. The sequence of the "repulsion" mode followed by the "rest" mode can be automated by the deactivation of the SPST switch in circuit 1 and the deactivation of the "after-delay SPST switch" in circuit 2. The after-delay switch first allows the SPDT to switch the Terminal A-Terminal B connection to the Terminal A-Terminal C connection. When battery terminal A is connected to terminal B, the current flow in circuit 2 is in the conventional direction, and now the magnetizable metal objects in circuit 2 (i.e., the magnetizable metals with an even number) have the same magnetic polarity as the magnetizable metals in circuit 1 (i.e., the magnetizable metals with an odd number). Therefore, these sequential neighboring magnetizable metals will repel one another if they are rods but attract one another if they are cylinders. The repulsion/attraction of the rods/cylinders can be swapped by transferring from one of battery 2 or battery 3 to the other. Overall, by clicking the "OFF" button of the device, the SPST in circuit 1 is disconnected, the SPDT switch switches between the two batteries in circuit 2, and finally the after-delay SPST switch in circuit 2 is also disconnected.

Because the cylinders have two "sets" of magnetizable metals each in a different semi-circumference, the "ON" button for it is programmed to have "ON" for the first set in one semi-circumference, followed by "ON" for the second set in the other semi-circumference, and the "OFF" button is programmed to have the same set of steps described above repeated twice, i.e. the after-delay SPST switch and the disconnection of both SPST switches in circuits 1 and 2 happens first for the first set in one semi-circumference then for the second set in the other semi-circumference.

In an embodiment, the electromagnet used to magnetize the magnetizable metal can allow the sphincter to handle pressures of about 1 mmHg to about 100 mmHg. This range of pressures is specifically selected to mimic the pressures excreted on sphincters in a body part, e.g., an internal urinary sphincter in the bladder.

For the avoidance of doubt, the present devices can be used not only in connection with the internal urinary sphincter of the bladder, but also in connection with any sphincter suffering from a partial or total loss of elasticity. Such other sphincters with which the present devices can be used include, by way of non-limiting example, the urinary sphincter of a bladder, the internal urethral sphincter, the external urethral sphincter, the upper esophageal sphincter, the lower esophageal sphincter, the pyloric sphincter, the sphincter of Oddi, the ileocecal sphincter, the internal anal sphincter, the external anal sphincter, and the precapillary sphincter.

In another embodiment, the present subject matter relates to a method for treating retrograde ejaculation in a patient, the method comprising: positioning a series of magnetizable metal objects to surround a wall of a bladder of the patient around a circumference of the internal urinary sphincter of the bladder; providing an energy source comprising at least two batteries to create at least a first electric current and a second electric current, respectively, to magnetize each magnetizable metal object; connecting the at least two batteries to alternating magnetizable metal objects of the series of magnetizable metal objects to provide at least a first circuit and a second circuit, respectively, the first circuit containing odd-numbered alternating magnetizable metal objects and the second circuit containing even-numbered alternating magnetizable metal objects as counted by starting from a first one of the alternating magnetizable metal objects which is considered alternating metal object number 1, the first metal object of the odd-numbered alternating magnetizable metal objects, the next one of the alternating magnetizable metal objects which is considered alternating metal object number 2, the first metal object of the even-numbered metal objects, and with each alternating metal object thereafter being among the odd-numbered alternating magnetizable metal objects or the even-numbered alternating magnetizable metal objects, accordingly, to provide the first electric current to each of the odd-numbered alternating magnetizable metal objects in the first circuit and the second electric current to each of the even-numbered alternating magnetizable metal objects in the second circuit; selectively activating each SPST with the at least two batteries in the first circuit and the second circuit enabling an attraction mode to provide the first electric current to each odd-numbered alternating magnetizable metal object and to provide the second electric current to each even-numbered alternating magnetizable metal object, thereby alternately magnetizing each odd-numbered alternating magnetizable metal object and each even-numbered alternating magnetizable metal object in attractive net magnetic polarities such that each magnetizable metal object of the series of magnetizable metal objects are attracted to each other to close the internal urinary sphincter in the bladder and prevent the retrograde ejaculation; if necessary, selectively activating each SPST switch to close each circuit and permit flow of the electric current while reversing polarity of each of the even-numbered alternating magnetizable metal objects to enable a repulsion mode to magnetize each of the odd-numbered alternating magnetizable metal objects and each of the even-numbered alternating magnetizable metal objects in repulsive net magnetic polarities such that each magnetizable metal object separates from one another to forcibly reopen the internal urinary sphincter of the bladder; and selectively deactivating each SPST switch to close each circuit and release the electric current such that each magnetizable metal object of the series of magnetizable metal objects demagnetize, permitting the magnetizable metal objects remain apart from one another, or to drift apart from one another, if the repulsion mode is skipped, due to a change in ambient conditions as described herein that pull the internal urinary sphincter of the bladder to an open position, thereby reopening the internal urinary sphincter in the bladder. In connection with the present methods, when the at least two batteries are selectively activated in the attraction mode, the internal urinary sphincter in the bladder is closed to selectively block retrograde ejaculation, preventing semen from entering the bladder of the patient and thereby preventing infertility of the patient.

In certain other embodiments, the method can further treat urinary incontinence in the patient.

It is to be understood that the device, system, and method are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A device for assisting in electromagnetically closing and reopening an internal urinary sphincter in a bladder of a patient, the device comprising:
a series of magnetizable metal objects configured to surround a wall of the bladder around a circumference of the internal urinary sphincter in the bladder;
an energy source comprising at least two batteries; and
a series of wires connecting the at least two batteries to alternating magnetizable metal objects of the series of magnetizable metal objects to provide at least a first circuit and a second circuit, respectively, with each battery in each of the first circuit and the second circuit being connected to a single-pole, single-throw (SPST) switch, thereby providing at least two total switches, which, when each SPST switch is activated, each respectively completes at least a first electric circuit allowing a first electric current and a second electric circuit allowing a second electric current, respectively, to separately magnetize each magnetizable metal object of the series of magnetizable metal objects, wherein each of the series of wires connecting the at least two batteries to alternating magnetizable metal objects of the series of magnetizable metal objects is covered with an insulating layer of biocompatible material to avoid causing an electric shock to the patient;
wherein the first circuit contains odd-numbered alternating magnetizable metal objects and the second circuit contains even-numbered alternating magnetizable metal objects as counted by starting from a first one of the alternating magnetizable metal objects which is considered alternating metal object number 1, the first metal object of the odd-numbered alternating magnetizable metal objects, the next one of the alternating magnetizable metal objects which is considered alternating metal object number 2, the first metal object of the even-numbered metal objects, and with each alternating metal object thereafter being among the odd-numbered alternating magnetizable metal objects or the even-numbered alternating magnetizable metal objects, accordingly;
wherein when each SPST switch in each circuit is activated to enable an attraction mode, each of the odd-numbered alternating magnetizable metal objects are magnetized and each of the even-numbered alternating magnetizable metal objects are magnetized with attractive magnetic polarities such that each magnetizable metal object of the series of magnetizable metal objects are configured to be attracted to each other to close the internal urinary sphincter in the bladder, wherein the SPST in the second circuit is an after-delay SPST switch;
wherein the second circuit further comprises a single-pole, double-throw (SPDT) switch configured to reverse polarity of each of the even-numbered magnetizable metal objects in the second circuit to enable a repulsion mode in which each of the odd-numbered alternating magnetizable metal objects and each of the even-numbered alternating magnetizable metal objects are magnetized with repulsive magnetic polarities such that each magnetizable metal object of the series of magnetizable metal objects are configured to separate from one another to forcibly reopen the internal urinary sphincter in the bladder to the internal urinary sphincter's original open position; and
wherein when each SPST switch in each circuit is deactivated to enable a rest mode, no electric current is conveyed to any of the magnetizable metal objects of the series of magnetizable metal objects.

2. The device for assisting in electromagnetically closing and reopening an internal urinary sphincter in a bladder of a patient of claim 1, wherein the magnetizable metal objects comprise an even number of eight or more magnetizable metal objects, wherein each magnetizable metal object in the series of magnetizable metal objects is configured to maintain the device, when at rest, in a ring configuration navigating along the circumference of the internal urinary sphincter in the bladder.

3. The device for assisting in electromagnetically closing and reopening an internal urinary sphincter in a bladder of a patient of claim 1, wherein each of the magnetizable metal objects in the series of magnetizable metal objects are magnetizable metal cylinders in a series of magnetizable metal cylinders and are configured to be embedded inside the wall of the bladder such that each of the magnetizable metal cylinders are maintained in a relatively constant position inside the wall of the bladder and navigating along the circumference of the internal urinary sphincter in the bladder such that when each alternating magnetizable metal cylinder has a same magnetic polarity with a next alternating magnetizable metal cylinder, such magnetizable metal cylinders are attracted to one another and when each alternating magnetizable metal cylinder has an opposite magnetic polarity with a next alternating magnetizable metal cylinder, such magnetizable metal cylinders repel one another.

4. The device for assisting in electromagnetically closing and reopening an internal urinary sphincter in a bladder of a patient of claim 3, wherein when each SPST switch in each circuit is activated to enable the attraction mode, a first set comprising a first half of each of odd-numbered and even-numbered alternating magnetizable metal cylinders of the series of magnetizable metal cylinders magnetize together to form a first line magnetized in a north-to-south direction and a second set comprising a second half of each of odd-numbered and even-numbered alternating magnetizable metal cylinders of the series of magnetizable metal cylinders magnetize together to form a second line magnetized in a south-to-north direction;

wherein the first line and the second line are configured to be attracted to each other to linearly close the internal urinary sphincter in the bladder;

wherein the first set and the second set each comprise separate first and second circuits, respectively.

5. The device for assisting in electromagnetically closing and reopening an internal urinary sphincter in a bladder of a patient of claim 4, wherein each of the first set and the second set are configured to define first and second semi-circular portions of the device, respectively, each of the first and second semi-circular portions of the device configured to be positioned around a first half and a second half of the circumference of the internal urinary sphincter in the bladder, respectively.

6. The device for assisting in electromagnetically closing and reopening an internal urinary sphincter in a bladder of a patient of claim 5, wherein the first set and the second set each comprises three batteries, wherein a first battery of the three batteries in each of the first set and the second set is in a first circuit of each of the first set and the second set, a second battery and a third battery of the three batteries in each of the first set and the second set is in a second circuit of each of the first set and the second set, and wherein the single-pole, double-throw (SPDT) switch and a separate single-pole, double throw switch in each of the first set and the second set, respectively, are configured to permit electric current to flow from the second battery in each of the first set and the second set to enable the attraction mode in each of the first set and the second set and to permit electric current to flow from the third battery in each of the first set and the second set to enable the repulsion mode in each of the first set and the second set.

7. The device for assisting in electromagnetically closing and reopening an internal urinary sphincter in a bladder of a patient of claim 4, wherein each of the odd-numbered alternating magnetizable metal objects and each of the even-numbered alternating magnetizable metal objects in each second circuit in each of the first set and the second sets are separately connected to the single-pole, double-throw switch and a separate single-pole, double-throw switch, respectively.

8. The device for assisting in electromagnetically closing and reopening an internal urinary sphincter in a bladder of a patient of claim 3, wherein each magnetizable metal cylinder has a diameter of up to 1.5 mm, configuring the device for closing the internal urinary sphincter in the bladder of the patient prevents at least one of retrograde ejaculation and urinary incontinence, and configuring the device for reopening the internal urinary sphincter in the bladder of the patient permits urine to release from the bladder.

9. The device for assisting in electromagnetically closing and reopening an internal urinary sphincter in a bladder of a patient of claim 1, wherein each of the magnetizable metal objects in the series of magnetizable metal objects are magnetizable metal rods in a series of magnetizable metal rods and are configured to be inserted through the wall of the bladder perpendicular to a plane of the internal urinary sphincter and navigating along the circumference of the internal urinary sphincter in the bladder such that when each alternating magnetizable metal rod has an opposite magnetic polarity with a next alternating magnetizable metal rod, such magnetizable metal rods are attracted to one another and when each alternating magnetizable metal rod has a same magnetic polarity with a next alternating magnetizable metal rod, such magnetizable metal rods repel one another, wherein each of the magnetizable metal rods have a stopper on each side of the wall so that each of the magnetizable metal rods are configured to have a fixed position and are configured to not be displaced and each of the magnetizable metal rods is configured to stick out of the wall of the bladder by about 1 mm on each side.

10. The device for assisting in electromagnetically closing and reopening an internal urinary sphincter in a bladder of a patient of claim 9, wherein when each SPST switch in each circuit is activated to enable the attraction mode, each magnetizable metal rod of the series of magnetizable metal rods are configured to be attracted focally to a center to close the internal urinary sphincter in the bladder.

11. The device for assisting in electromagnetically closing and reopening an internal urinary sphincter in a bladder of a patient of claim 1, wherein the SPDT switch is removed and the at least two batteries comprise two batteries, with a first of the two batteries providing the first electric current to the first circuit and the second of the two batteries providing the second electric current to the second circuit, thereby preventing enablement of the repulsion mode, and wherein the reopening of the internal urinary sphincter occurs in rest mode based on ambient conditions.

12. The device for assisting in electromagnetically reopening an internal urinary sphincter in a bladder of a patient of claim 1, wherein the at least two batteries comprise two batteries, and wherein a first battery of the two batteries is configured to replace electrical current provided by a third battery to instead be provided by the first battery, thereby enabling the repulsion mode.

13. The device for assisting in electromagnetically closing and reopening an internal urinary sphincter in a bladder of a patient of claim 1, wherein the at least two batteries comprise three batteries configured such that every odd-numbered alternating magnetizable metal object of the series of magnetizable metal objects is connected to a first battery of the three batteries, in parallel;

every even-numbered alternating magnetizable metal object of the series of magnetizable metal objects is connected to a second battery and a third battery of the three batteries, in parallel;

wherein the single-pole, single-throw (SPST) switch in the first circuit connects the first battery to every odd-numbered alternating magnetizable metal object of the series of magnetizable metal objects;

wherein the single-pole, single throw (SPST) switch in the second circuit connects the second electric current flowing from the second battery or a third battery through the single-pole, double-throw (SPDT) switch to every even-numbered alternating magnetizable metal object of the series of magnetizable metal objects;

wherein the single-pole, double-throw (SPDT) switch switches the second electric current to flow from either the second battery or the third battery to every even-numbered alternating magnetizable metal object of the series of magnetizable metal objects;

wherein when the single-pole, single-throw (SPST) switch in each circuit is activated to enable the attraction mode, the single-pole, single-throw (SPST) switch in the first circuit permits the first electric current to flow from the first battery to every odd-numbered alternating magnetizable metal object of the series of magnetizable metal objects, and the single-pole, single-throw (SPST) switch in the second circuit permits the second electric current to flow from the second battery to every even-numbered alternating magnetizable metal object of the series of magnetizable metal objects in attractive magnetic polarities such that each magnetizable metal object of the series of magnetizable metal objects is configured to be attracted to each other to close the internal urinary sphincter in the bladder;

wherein when the single-pole, single-throw (SPST) switch in each circuit is activated and the SPDT switch in the second circuit reverses polarity of each of the even-numbered magnetizable metal objects of the series of magnetizable metal objects in the second circuit to enable the repulsion mode, the single-pole, single-throw (SPST) switch in the first circuit permits the first electric current to flow from the first battery to every odd-numbered alternating magnetizable metal object of the series of magnetizable metal objects and the single-pole, single-throw (SPST) switch in the second circuit permits the second electric current to flow from the third battery to every even-numbered alternating magnetizable metal object of the series of magnetizable metal objects to provide repulsive magnetic polarities such that each magnetizable metal object of the series of magnetizable metal objects is configured to be separated from one another to forcibly reopen the internal urinary sphincter in the bladder; and wherein when the SPST switch in each circuit is deactivated to enable the rest mode, the first electric current in the first circuit and the second electric current in the second circuit are not permitted to flow such that no electric current is conveyed to each of the magnetizable metal objects of the series of magnetizable metal objects, allowing the magnetizable metal objects of the series of magnetizable metal objects to move apart from one another due to a change in ambient conditions that pull the internal urinary sphincter in the bladder to an open position.

14. The device for assisting in electromagnetically closing and reopening an internal urinary sphincter in a bladder of a patient of claim 13, wherein each of the first battery, second battery, and third battery is a wirelessly rechargeable battery or a replaceable battery configured to be placed subcutaneously in the patient, and wherein the at least one battery and the at least one SPST switch are operated via a wireless remote control, Bluetooth, or through a wirelessly connected cellphone, wearable band, or watch, wherein the attraction mode is selectively activated by pressing an "ON" button of the device and the repulsion mode, followed by the rest mode as automatically programmed to be executed via the after-delay switch, is selectively activated by pressing an "OFF" button of the device, wherein the "ON" button of the device is programmed to be executed once for each set of magnetizable metal objects of the series of magnetizable metal objects.

15. The device for assisting in electromagnetically closing and reopening an internal urinary sphincter in a bladder of a patient of claim 1, wherein when the attraction mode is enabled, the device allows the internal urinary sphincter to handle a pressure of about 1 mmHg to about 100 mmHg to mimic pressures exerted on properly functioning internal urinary sphincters.

16. The device for assisting in electromagnetically closing and reopening an internal urinary sphincter in a bladder of a patient of claim 1, wherein the magnetizable metal in the series of magnetizable metal objects is martensitic stainless steel or a cobalt-chromium alloy.

17. The device for assisting in electromagnetically closing and reopening an internal sphincter in a body part of a patient of claim 1, wherein the device is configured to close a sphincter of the patient selected from the group consisting of a urinary sphincter of a bladder, an internal urethral sphincter, an external urethral sphincter, an upper esophageal sphincter, a lower esophageal sphincter, a pyloric sphincter, a sphincter of Oddi, an ileocecal sphincter, an internal anal sphincter, an external anal sphincter, and a precapillary sphincter.

18. A method for treating retrograde ejaculation in a patient, the method comprising:
positioning a series of magnetizable metal objects to surround a wall of a bladder of the patient around a circumference of the internal urinary sphincter at the neck of the bladder;
providing an energy source comprising at least two batteries to create at least a first electric current and a second electric current, respectively, to magnetize each magnetizable metal object of the series of magnetizable metal objects;
connecting the at least two batteries to alternating magnetizable metal objects of the series of magnetizable metal objects to provide at least a first circuit and a second circuit, respectively, the first circuit containing odd-numbered alternating magnetizable metal objects and the second circuit containing even-numbered alternating magnetizable metal objects as counted by starting from a first one of the alternating magnetizable metal objects which is considered alternating metal object number 1, the first metal object of the odd-numbered alternating magnetizable metal objects, the next one of the alternating magnetizable metal objects which is considered alternating metal object number 2, the first metal object of the even-numbered metal objects, and with each alternating metal object of the series of magnetizable metal objects thereafter being among the odd-numbered alternating magnetizable metal objects or the even-numbered alternating magnetizable metal objects, accordingly, to provide the first electric current to each of the odd-numbered alternating magnetizable metal objects of the series of magnetizable metal objects in the first circuit and the second electric current to each of the even-numbered alternating magnetizable metal objects of the series of magnetizable metal objects in the second circuit;

selectively activating a single-pole, single-throw transfer switch (SPST) connected to batteries of the at least two batteries in each of the first circuit and the second circuit to enable an attraction mode to provide the first electric current to each odd-numbered alternating magnetizable metal object of the series of magnetizable metal objects and to provide the second electric current to each even-numbered alternating magnetizable metal object of the series of magnetizable metal objects, thereby alternately magnetizing each odd-numbered alternating magnetizable metal object of the series of magnetizable metal objects and each even-numbered alternating magnetizable metal object of the series of magnetizable metal objects with attractive magnetic polarities such that each magnetizable metal object of the series of magnetizable metal objects are attracted to each other to close the internal urinary sphincter in the bladder and prevent the retrograde ejaculation;

if each of the magnetizable objects in the series of magnetizable metal objects do not drift apart from one another due to a change in ambient conditions, selectively activating each SPST connected to the at least two batteries in each of the first circuit and the second circuit while reversing polarity of each of the even-numbered alternating magnetizable metal objects of the series of magnetizable metal objects by flipping a single-pole double-transfer (SPDT) switch, to enable a repulsion mode to magnetize each of the odd-numbered alternating magnetizable metal objects of the series of magnetizable metal objects and each of the even-numbered alternating magnetizable metal objects of the series of magnetizable metal objects with repulsive magnetic polarities such that each magnetizable metal object of the series of magnetizable objects separates from one another to forcibly reopen the internal urinary sphincter of the bladder, thereby allowing urine to exit the bladder; and selectively deactivating each SPST switch connected to the batteries in each of the first circuit and the second circuit to release the electric current such that each magnetizable metal object of the series of magnetizable metal objects demagnetize, permitting the magnetizable metal objects to remain in the open position if the repulsion mode was enabled before the rest mode, or to move apart from one another due to a change in ambient conditions that pull the internal urinary sphincter of the bladder to an open position in case the repulsion mode was not enabled before the rest mode, thereby reopening the internal urinary sphincter in the bladder.

19. The method of claim 18, wherein when the at least two batteries are selectively activated in the attraction mode, the internal urinary sphincter in the bladder is closed to selectively block retrograde ejaculation, preventing semen from entering the bladder of the patient and thereby preventing infertility of the patient.

20. The method of claim 18, wherein the method further treats urinary incontinence in the patient.

* * * * *